United States Patent [19]

Shepherd

[11] Patent Number: 4,485,105

[45] Date of Patent: Nov. 27, 1984

[54] METHOD OF TREATING HYPERLIPIDEMIA WITH 4-(MONOALKYLAMINO)BENZOIC ACID AMIDES

[75] Inventor: Robert G. Shepherd, South Nyack, N.Y.

[73] Assignee: American Cyanamid Company, Stamford, Conn.

[21] Appl. No.: 154,741

[22] Filed: May 30, 1980

Related U.S. Application Data

[60] Continuation-in-part of Ser. No. 950,899, Oct. 12, 1978, Pat. No. 4,242,273, which is a division of Ser. No. 836,949, Sep. 27, 1977, Pat. No. 4,136,256.

[51] Int. Cl.³ .................. A61K 31/33; A61K 31/535; A61K 31/44; A61K 31/445; A61K 31/18; A61K 31/425; A61K 31/40; A61K 31/135; A61K 31/165

[52] U.S. Cl. ................. 424/248.54; 424/244; 424/248.5; 424/248.57; 424/263; 424/267; 424/270; 424/272; 424/274; 424/321; 424/324; 424/330

[58] Field of Search ............ 424/267, 274, 244, 248.5, 424/248.54, 248.57, 263, 267, 270, 272, 274, 330, 321, 324; 260/453 RW

[56] References Cited

U.S. PATENT DOCUMENTS 4,136,256  1/1979  Shepherd .................. 544/88
4,242,273  12/1980  Shepherd .................. 260/453 RW Primary Examiner—Anna P. Fagelson
Attorney, Agent, or Firm—Edward A. Conroy, Jr.

[57] ABSTRACT

This disclosure describes a method of treating hyperlipidemia and atherosclerotic lesions with 4-(monoalkylamino)benzoic acid amides and compositions therefor.

22 Claims, No Drawings

METHOD OF TREATING HYPERLIPIDEMIA WITH 4-(MONOALKYLAMINO)BENZOIC ACID AMIDES

CROSS REFERENCE TO RELATED APPLICATION

This application is a continuation-in-part application of my copending application Ser. No. 950,899 now U.S. Pat. No. 4,242,273, filed Oct. 12, 1978, which in turn is a division of my copending application Ser. No. 836,949 filed Sept. 27, 1977 now U.S. Pat. No. 4,136,256.

BRIEF SUMMARY OF THE INVENTION

This invention relates to a method of treating hyperlipidemia and atheroscloeritc lesions with 4-(monoalkylamino)benzoic acid amides which may be represented by the following structural formula:

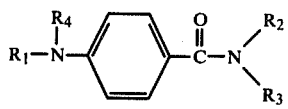

wherein $R_1$ is a straight chain or branched alkyl group of the formula $C_nH_{2n+1}$ wherein n is an integer from 8 to 19, inclusive; $R_2$ is selected from the group consisting of hydrogen, lower alkyl, carboxy lower alkyl, carboalkoxy lower alkyl, lower alkanoyl, carbamoyl, di(-lower alkyl)carbamoyl, lower alkanesulfonyl, benzenesulfonyl, sodium sulfo lower alkyl, sulfo lower alkyl, lower alkenyl, lower alkynyl, cyclohexyl, phenyl lower alkyl and ω-hydroxy lower alkyl; $R_3$ is selected from the group consisting of hydrogen, lower alkyl, hydroxy, lower alkoxy, halo lower alkyl, phenyl, carboxyphenyl, chlorophenyl, sodium sulfophenyl, pyridyl, pyridyl lower alkyl, mono- and poly-hydroxy lower alkyl, ω-lower alkoxy lower alkyl, ω-di(lower alkyl)amino lower alkyl, ω-piperidino lower alkyl, ω-pyrrolidino lower hydroxy alkyl, amino, di(lower alkyl)amino, lower alkanoylamino, lower alkanesulfonylamino, N-piperidyl, benzenesulfonylamino, and 4-lower alkyl-1-piperazino; and $R_2$ and $R_3$ taken together with the associated N(itrogen) is selected from the group consisting of pyrrolidino, piperidino, morpholino, hexamethyleneimino, 4-lower alkylpiperidino, 4-lower alkyl-1-piperazino, 4-phenylpiperazino, 3-pyrrolinyl, $\Delta^3$-piperidino, 4-(carboethoxy or carboxy)-3-thiazolidinyl, and 4-carboethoxy-3-oxazolidinyl; and $R_4$ is hydrogen or a group convertible in vivo thereinto such as methyl, ethyl, carboxymethyl, lower alkanoyl ($C_1$-$C_6$), succinyl, 1-(sodium sulfo)lower alkyl, 1-(sodium sulfo)-polyhydroxyalkyl or 1,3-bis-(sodium sulfo)aralkyl.

Suitable lower alkyl and lower alkoxy groups contemplated by the present invention are those having up to 4 carbon atoms such as, for example, methyl, ethyl, iso-propyl, sec-butyl, methoxy, ethoxy, n-propoxy, tert-butoxy, etc. Halo is exemplified by chloro, bromo or iodo whereas pyridyl may be α-, β-, or γ-pyridyl. Suitable phenyl lower alkyl and pyridyl lower alkyl groups thus may be, for example, benzyl, β-phenylethyl, α-pyridylmethyl, β-(γ-pyridyl)ethyl and the like. Appropriate mono- and poly-hydroxy lower alkyl and ω-lower alkoxy lower alkyl groups may be hydroxymethyl, β-hydroxyethyl, 3-hydroxypropyl, 2,3-dihydroxypropyl, α- and β-ethoxyethyl, and the like. Suitable carboxyalkyl and sulfoalkyl groups may be, for example, carboxymethyl, β-carboxyethyl, α-carboxypropyl, 2-sulfoethyl, 2-sulfopropyl, and the like. Appropriate alkanesulfonyl groups are methanesulfonyl, ethanesulfonyl, propanesulfonyl, and the like. Suitable lower alkenyl and lower alkynyl groups contemplated by the present invention are those having up to four carbon atoms and attached to the nitrogen atom via a carbon atom that is not part of an unsaturated bond such as, for example, allyl, 2-butenyl, 3-butenyl, isobutenyl, 2-butynyl, propargyl, etc.

Suitable branched alkyl groups for the substituent $R_1$ may be, for example, 1-methylpentadecyl, 1-ethyltetradecyl, 1-heptylnonyl, 2-ethyldodecyl, 1,4-diethyloctyl, 11-methyldodecyl, 5,5-dimethylhexyl, 4,8,12-trimethyltridecyl, 2,4,6,8-tetramethylnonyl, 1,4-dimethyl-1-ethylhexyl, and the like.

The invention also pertains to novel compositions of matter useful as anti-atherosclerotic agents and to methods of meliorating atherosclerosis by counteracting hyperlipemia and arterial plaque formation in mammals therewith; the active ingredients of said compositions of matter being the 4-(monoalkylamino)benzoic acid amides. These compounds may be utilized either as the free bases or in the form of a pharmaceutically acceptable salt with an organic or inorganic acid or base. The compounds used in the present invention are claimed as such in my copending application Ser. No. 950,899.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in their initiation and development and also, most importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon & Verter, Annals of Internal Medicine, pp 1–12, 1971) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson & Bottiger, Lancetii, pp 865–868, 1972) to carry the highest risk of coronary heart disease. The majority of patients with ischemic heart disease or peripheral vascular disease were found to have hyperlipoproteinemia, involving very low-density and/or low-density lipoproteins (Lewis et al. British Medical Journal, Vol. 3, pp 489, 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine and nicotinic acid [(Levy & Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Orally active agents are required since patients usually take them for a number of years.

DETAILED DESCRIPTION OF THE INVENTION

The compounds used in this invention are amides of the 4-(monoalkylamino)benzoic acids described in U.S. Pat. No. 3,868,416 and have useful biological and pharmacological properties. No hypolipidemic activity has been reported in the literature for these compounds and they are different in structure from other hypolipidemic agents. The compounds used in this invention lower serum-lipid concentrations and also minimize atheroma formation in the aorta. These amides provide the oral administration required of hypolipidemic agents, which patients usually take for many years. To the extent that these compounds which are innocuous or are natural components of mammalian physiological processes. The amides are quite adequately and reliably absorbed from the gastrointestinal tract and cause less gastrointestinal irritation than the corresponding carboxylic acids.

We have now found that members of this class of compound can safely and effectively lower both serum sterols and triglycerides in warm-blooded animals. Such actions on serum lipid components are considered to be very useful in the treatment of atherosclerosis, especially in contrast to available drugs whose action in much more limited. For some time it has been considered desirable to lower serum lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm blooded mammals for the treatment of hyperlipidemic and atherosclerotic states found in patients with or prone to heart attacks, to peripheral or cerebral vascular disease, and to stroke.

The compounds used in this invention are, in general, white to tan crystalline solids having characteristic melting points and basorption spectra. They are soluble in organic solvents such as lower alkanols, chloroform, benzene, dimethylformamide, and the like but are generally not very soluble in water. The compounds of the present invention, which are organic bases, may be converted to their non-toxic acid-addition salts with a variety of pharmaceutically acceptable organic and inorganic salt-forming reagents. Thus, acid-addition salts may be formed by admixture of the organic free base in a neutral solvent with one or two equivalents of an acid such as sulfuric, phosphoric, hydrochloric, hydrobromic, trifluoroacetic, citric, succinic, tartaric, gluconic, ascorbic, and the like. The amides which contain acidic groups form pharmaceutically acceptable cationic salts with bases such as the alkali metal hydroxides, the alkaline earth metal hydroxides, and the like.

The compounds of the present invention may be readily prepared as disclosed in my copending application Ser. No. 950,899 and in my issued patent, U.S. Pat. No. 4,136,256, both incorporated herein by reference thereto.

Certain derivatives

of the aminobenzoyl nitrogen atom are useful for providing greater solubility, more uniform and reliable intestinal absorption, and for a certain degree of modification of the pharmacology of the compounds of the present invention. Some of these derivatives can be converted to the corresponding N-H forms by the acidity of the stomach or the alkalinity of the small intestine. Others are converted by metabolic processes.

The compounds of the present invention are not only potent hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered conveniently by the oral route. It is not known how these novel compounds operate in the blood serum and no theory of why these compounds so operate is advanced. It is not intended that the present invention should be limited to any particular mechanism of action of lowering serum lipids or of meliorating atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: A binder such as gum tragacanth, acacia, corn starch or gelatin; excipients such as dicalcium phosphate,; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active ingredients may be incorporated into sustained-release preparations and formulations.

A preferred embodiment of the present invention resides in the method of treatment herein using the compounds represented by the following structural formula:

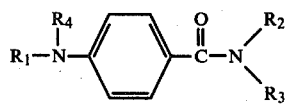

wherein $R_1$ is a straight chain or branched alkyl group of the formula $C_nH_{2n+1}$ wherein n is an integer from 8 to 19, inclusive; $R_2$ is hydrogen; $R_3$ is alkyl having up to 3 carbon atoms and substituted with 1 or 2 hydroxy groups, alkanoyl having up to 3 carbon atoms, hydroxy, alkoxy having up to 3 carbon atoms, carboxy lower alkyl, carbomethoxy lower alkyl, carbethoxy lower alkyl, sulfo lower alkyl, alkanesulfonyl having up to 3 carbon atoms, phenylsulfonyl, alkanesulfonamido having up to 3 carbon atoms, phenylsulfonamido, sulfophenyl or carboxyphenyl; and $R_2$ and $R_3$ taken together is $-(CH_2)_{4-6}-$ optionally substituted with hydroxy, carboxy, hydroxymethyl or up to 3 methyl groups; and $R_4$ is hydrogen or a group convertible thereinto in vivo as hereinabove defined. A more preferred embodiment is as immediately above except that $R_4$ is hydrogen only.

A most preferred embodiment of the present invention resides in the method of treatment herein using the compounds represented by the following structural formula:

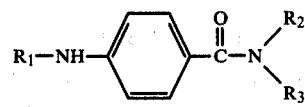

wherein $R_1$ is a straight chain or branched alkyl group of the formula $C_nH_{2n+1}$ wherein n is an integer from 8 to 19, inclusive; $R_2$ is hydrogen; $R_3$ is alkyl having up to 3 carbon atoms and substituted with 1 or 2 hydroxy groups, acetyl, hydroxy, carboxy lower alkyl, sulfo lower alkyl, methanesulfonyl, phenylsulfonyl, methylsulfonamido or acetylamino; and $R_2$ and $R_3$ taken together is $-(CH_2)_4-$ optionally substituted with hydroxy, carboxy, hydroxymethyl or up to 2 methyl groups.

The invention will be described in greater detail in conjunction with the following specific examples.

EXAMPLE 1

Preparation of 4-(hexadecylamino)benzamide

Three-tenths of a mole of 4-(hexadecylamino)benzoic acid (10.9 gm.) was heated in 450 ml. of anhydrous methylene chloride at 40° C. Anhydrous HCl was then bubbled into the clear s-lution for one hour and the solids were collected. The solids were then added to a dry three-neck flask and 110 ml. of SOCl (184 gm.) added forming a thick slurry which was stirred for nineteen hours at room temperature. The material was then concentrated to dryness, diluted with 250 ml. of methylene chloride, cooled to 0° C. and anhydrous ammonia added over an hour. The reaction was then kept at −5° C. for twenty one hours, the solids collected and washed with 25 ml. each of methylene chloride, ethanol, and water. The solids were then recrystallized from 200 ml. of ethanol and again from ethyl acetate (100 ml.). The TLC showed one spot (benzene/acetic acid) and analysis by NMR was in agreement with the assigned structure.

EXAMPLE 2

Preparation of 4-(hexadecylamino)benzoyl chloride hydrochloride

A cold solution of 25 g. of 4-(hexadecylamino)benzoic acid in 500 ml. of dimethoxyethane-methylene chloride (4:1) is prepared and dry hydrochloric acid is bubbled through the solution until no more precipitate forms. The solution is treated with 25 ml. of thionyl chloride and refluxed until all of the precipitate was re-dissolved. The solvents are evaporated to yield an orange, semi-crystalline mass.

EXAMPLE 3

Preparation of N,N-dimethyl-4-(hexadecylamino)benzamide

In a solution of 100 ml. of methylene dichloride and 25 ml. of glyme was dissolved in 10 ml. of thionyl chloride and 4.0 g of 4-(n-hexadecylamino)benzoic acid hydrochloride. The reaction mixture was heated to the reflux temperature for 2 hours and then cooled to room temperature. To this solution of acid chloride was added a solution of 200 ml. of diethyl ether, 25 ml. of glyme, and 0.1 g of 4-dimethylaminopyridine which had been saturated with dimethylamine gas. This reaction mixture was stirred at room temperature for 2 hours whereby there was obtained a 92% yield of product, melting point 70°-72° C.

EXAMPLE 4

Preparation of 4-(hexadecylamino)benzoyl piperidide

To a chilled solution of 35 ml. of piperidine, 2.5 ml. of triethylamine and 0.6 g. of dimethylaminopyridine in 100 ml. of diethyl ether was added (½ hour) a solution of 8.3 g. of 4-hexadecylaminobenzoyl chloride in 50 ml. of ether. The solution was warmed to room temperature and maintained there for two hours. The solution was heated to reflux for an additional 2 hours at which time the reaction was complete. The solution was cooled, extracted twice with 100 ml. portions of water and dried over $MgSO_4$. The solvent was removed in vacuo and the solid was recrystallized in 50 ml. of diethyl ether giving 5.8 g. (74%).

EXAMPLE 5

Preparation of β-phenethyl-4-(hexadecylamino)benzamide

To a chilled solution of 0.1 g. of 4-dimethylaminopyridine, 5.7 g. of β-phenethylamine and 13 ml. of triethylamine in 55 ml. of dimethoxyethane (glyme) at 10° C. was added 7.4 g. of 4-hexadecylaminobenzoyl chloride hydrochloride in 45 ml. of glyme. The reaction was allowed to warm to room temperature and then refluxed for 2.5 hours. An I.R. showed no acid chloride band at this time. The solution was cooled overnight and filtered giving 9.35 g. of an off-white material. This material was recrystallized from 400 ml. of 90% acetone ($H_2$) giving 4.45 g. and 0.76 g. in two crops (26%). An aliquot (0.5 g.) was recrystallized from 29 ml. of cyclohexane giving 0.44 g. melting point 125°-127° C.

EXAMPLE 6

Preparation of ethyl 4-(hexadecylamino)hippurate

To a solution of 18.08 g. of 4-(hexadecylamino)benzoic acid in a mixture of dioxane and $CH_2Cl_2$ (40 ml./160 ml.) was added gaseous HCl for 10 minutes. The slurry was cooled and 18 ml. of $SOCl_2$ added. The slurry was brought to reflux for 2 hours and then concentrated under vacuum (thrice diluting with dioxane each time). The final amber solution was diluted with 100 ml. of dioxane and this solution added to freshly prepared ethyl glycinate in 300 ml. of $CH_2Cl_2$ containing 1 g. of dimethylaminopyridine and 10 ml. of triethylamine. After 16 hours at room temperature the reaction appeared complete but was refluxed for 2 hours, cooled and filtered. The mother liquor was extracted with $H_2O$ and 10% HCl. The solution was dried over $MgSO_4$ and concentrated in vacuo to an amber liquid, 18.97 g. A 6 g. sample was preabsorbed on 30 g. of silica III and placed on 450 g. of silica giving 4.2 g. of solid which was placed on 250 ml. of alumina and eluted with ether giving 4.2 g. of solid. TLC (hexane:ethylacetate, 3:1) indicated three spots so this material (3 g.) was placed on a second silica column giving a solid (1.0 g.) which was recrystallized from 50 ml. of acetonitrile giving 0.6 g., melting point 97.5°-99.5° C.

EXAMPLE 7

Preparation of N-[4-(hexadecylamino)benzolyl]glycine

A mixture of 26.5 g (0.100 mole) of ethyl N-[4-(hexadecylamino)benzoyl]glycinate, 110 ml. of 1N sodium hydroxide solution; and 100 ml. of ethanol was stirred at ambient temperature for 2 hours and then partially evaporated. The aqueous solution was washed with diethyl ether, acidified with 6N hydrochloric acid, and filtered. The white solid was dried in vacuo and recrystallized from acetone, melting point 192°-194° C.

EXAMPLE 8

Preparation of N-[4-(hexadecylamino)benzoyl]-2-methylalanine

A mixture of 5.24 g. of α-aminoisobutyric acid, 50 ml. of pyridine, and 25 ml. of $H_2O$ was stirred while 21.1 g. of 4-(hexadecylamino)benzoyl chloride hydrochloride was added. The mixture was stirred for 18 hours at ambient temperature and filtered. The filtrate was evaporated and the residual yellow glass was dissolved in 1N NaOH solution. The solution was extracted with diethyl ether and then acidified with 6N HCl. The precipitate was collected, dried, and recrystallized from acetone, melting point 199°-202° C.

EXAMPLE 9

Preparation of N-[4-(hexadecylamino)benzoyl]trifluoromethanesulfonamide

A solution of 1.25 g. of trifluoromethanesulfonamide in 35 ml. of pyridine was treated with 3.5 g of 4-(hexadecylamino)benzoyl chloride hydrochloride in methylene chloride at 10°-15° C. and then stirred under reflux for 3 hours. Evaporation afforded a gum which was stirred with 150 ml. of $H_2O$ and extracted with three 50 ml. portions of $CHCl_3$. The extracts were combined, dried ($MgsO_4$), and evaporated to yield a white solid. Crystallization from ether-acetone gave 2.0 g. of product, melting point 172°-174° C.

EXAMPLE 10

Preparation of N-[4-(hexadecylamino)benzoyl]-4-t-butylbenzenesulfonamide

A solution of 21.1 g. of 4-(hexadecylamino)benzoyl chloride hydrochloride and 10.8 g. of p-tert-butylbenzenesulfonamide in 250 ml. of pyridine was stirred under reflux for 2 hours and evaporated. The residue was partitioned between 1N hydrochloric acid and $CH_2Cl_2$ and the organic layer was separated, washed with water, dried ($MgSO_4$), and evaporated. Crystallization of the residual glass from $CH_2Cl_2$ hexane afforded a white solid, melting point 173°-176° C.

EXAMPLE 11

Preparation of p-hexadecylamino-N-(p-nitrophenylsulfonyl)benzamide

A solution of 40.4 g of p-nitrobenzenesulfonamide in 250 ml. of dry dimethylacetamide is added dropwise, over 30 minutes, to a stirred and cooled (water bath) suspension of 5.5 g. of sodium hydride in 100 ml. of dry dimethylacetamide. The resulting dark solution is stirred for a further 30 minutes at room temperature. In the meantime, a mixture of 36.2 g. of p-hexadecylaminobenzoic acid in 1200 ml. of methylene chloride, 300 ml. of dimethoxyethane, and 40 ml. of thionyl chloride is refluxed for 1 hour and 15 minutes. The solution is evaporated to an oil which is co-evaporated twice with added dioxane to remove excess thionyl chloride. The resulting amber oil is dissolved in 75 ml. of dry dimethylacetamide and the solution is added, over approximately 3 minutes, to the previously prepared solution of sodium p-nitrobenzenesulfonamide and cooled in an ice bath. After the addition, the ice bath is removed and the solution is stirred at room temperature for one hour. The solution is filtered through a bed of diatomaceous earth and the filtrate is poured into 2.1 of water to give a suspension. Saturated sodium chloride solution (250 ml.) followed by sodium chloride crystals (100 g.) is added to produce a finely divided precipitate. The mixture is filtered through a bed of diatomaceous earth. The product is washed with water and partially dried on the filter to give a yellow paste. The paste is dissolved in a mixture of 250 ml. of methylene chloride, 250 ml. of ethyl acetate, and 250 ml. of acetone. The solution is filtered through a bed of diatomaceous earth, a small aqueous layer separated, and the organic phase dried over anhydrous sodium sulfate. The solution is filtered and the filtrate is evaporated to an amber glass which is crystallized from 150 ml. of 1:1 ether:hexane. The product was recrystallized three times from absolute ethanol to provide 14.75 g. of the title compound as bright yellow crystals, melting point 129.5°–131° C.

EXAMPLE 12

Preparation of
p-Hexadecylamino-N-Sulfanilylbenzamide

A solution of p-hexadecylamino-N-(p-nitrophenylsulfonyl)benzamide in 150 ml. of tetrahydrofuran is hydrogenated in the presence of 0.9 g. of 10% palladium on carbon catalyst at approximately 50 lbs. for 22 hours. The mixture is filtered through a bed of diatomaceous earth and the filtrate is evaporated to an incompletely reduced, off-white solid as indicated by thin layer chromatography on silica gel using chloroform:ethyl acetate:acetic acid 95:4:1 as solvent. The product is hydrogenated again in 80 ml. of dimethylformamide plus 1.0 g. of 10% palladium on carbon catalyst for 18 hours at 50 lbs. pressure. The mixture is filtered through a bed of diatomaceous earth and the filtrate is diluted with 500 ml. of eater to give a suspension which is coagulated by the addition of 50 g. of sodium chloride. The mixture is filtered, the product is washed thoroughly with water and dried in a dessicator to give 8.35 g. of product which is a single spot of TLC. The product is crystallized twice from ethyl acetate and dried in an Abderhalden pistol at 65° C. to provide 6.45 g. of pale tan crystals, melting point 193°–196° C.

EXAMPLE 13

Preparation of
p-hexadecylamino-N-(phenylsulfonyl)benzamide

A solution of 31.4 g. of benzenesulfonamide in 250 ml. of dry dimethylacetamide is added dropwise, with stirring and cooling, to a suspension of 5.5 g. of sodium hydride in 100 ml. of dry dimethylacetamide over 30 minutes at room temperature. Stirring is continued for a further 30 minutes. In the meantime, a mixture of 36.2 g. of p-hexadecylaminobenzoic acid in 1200 ml. of methylene chloride, 300 ml. of dimethoxyethane, and 40 ml. of thionyl chloride is refluxed for 1 hour and 15 minutes. The solution is evaporated to an oil which is co-evaporated twice with added dioxane to remove excess thionyl chloride. To the resulting oily residue of p-hexadecylaminobenzoyl chloride hydrochloride is added, in one portion, the previously prepared mixture of sodium benzene-sulfonamide in dimethylacetamide. The mixture is stirred for 30 minutes, without cooling, and is then filtered through a bed of diatomaceous earth. The filtrate is poured into 2 l. of water, and 250 ml. of saturated sodium chloride solution is added to coagulate the precipitate. The mixture is filtered and the product is washed with water and partially air dried. The product is dissolved in methylene chloride, the mixture is filtered through diatomaceous earth, and brine is added to break the emulsion. The layers are separated, the organic phase is dried over anhydrous sodium sulfate and filtered through a bed of 300 g. of hydrous magnesium silicate. The product is eluted with an additional 3 l. of methylene chloride. The first approx. 1 l. of filtrate is set aside and the remainder is evaporated to dryness. The residue is crystallized three times from toluene and the product is dried in the Abderhalden at 65° C. to provide 10.8 g. of the title compound as colorless crystals melting point 136°–137.5° C.

EXAMPLE 14

Preparation of
p-Hexadecylamino-N-(methylsulfonyl)benzamide

A solution of 19.0 g. of methanesulfonamide in 150 ml. of dry dimethylacetamide is added dropwise over 15 minutes to a stirred and cooled (water bath) suspension of 5.5 g. of sodium hydride in 100 ml. of dry dimethylacetamide. The mixture is then stirred and heated at 60°–80° C. for 2 hours. In the meantime, a mixture of 36.2 g. of p-hexadecylaminobenzoic acid in 1200 ml. of methylene chloride, 300 ml. of dimethoxyethane, and 40 ml. of thionyl chloride is refluxed for 1 hour and 15 minutes. The solution is evaporated to an oil which is co-evaporated twice with added dioxane to remove excess thionyl chloride. To the resulting oily residue of p-hexadecylaminobenzoyl chloride hydrochloride is added, in one portion, the previously prepared mixture of sodium methanesulfonamide in dimethylacetamide. The mixture becomes very hot and is cooled briefly in a water bath and then is stirred at room temperature for 30 minutes. The mixture is filtered through a bed of diatomaceous earth and the filtrate is poured into 2 l. of water. The resulting suspension is coagulated by the addition of 250 ml. of saturated sodium chloride solution and the mixture is filtered. The product is washed with water, partially air dried and then crystallized from 1.5 l. of ethanol. The product is recrystallized twice from p-dioxane and dried in the Abderhalden at 65° C. to give 12.0 g. of the title compound as tan crystals melting point 173°–175° C.

EXAMPLE 15

Preparation of
p-Hexadecylamino-N-(p-tolylsulfonyl)benzamide

A solution of 34.25 g. of p-toluenesulfonamide in 250 ml. of dry dimethylacetamide is added dropwise over 30 minutes to a stirred and cooled (water bath) suspension of 5.5 g. of sodium hydride in 100 ml. of dry dimethylacetamide. Stirring is continued at room temperature for 3 hours until foaming subsides. In the meantime, a mixture of 36.2 g. of p-hexadecylaminobenzoic acid in 1200 ml. of methylene chloride, 300 ml. of dimethoxyethane, and 40 ml. of thionyl chloride is refluxed for 1 hour and 15 minutes. The solution is evaporated to an oil which is co-evaporated twice with added dioxane to remove excess thionyl chloride. To the resulting oily residue of p-hexadecylaminobenzoyl chloride is added, in one portion, the previously prepared mixture of sodium p-toluenesulfonamide in dimethylacetamide. The mixture is stirred for 30 minutes, without cooling, and is filtered through a bed of diatomaceous earth. The filtrate is poured into 2 l. of water and the resulting suspension is coagulated by the addition of 250 ml. of saturated sodium chloride solution. The gummy solid is decanted and the product is dissolved in 700 ml. of methylene chloride. The mixture is filtered through diatomaceous earth and brine is added to break the emulsion. The layers are separated and the organic phase is dried over anhydrous sodium sulfate and filtered. The filtrate is concentrated on the steam bath to approx. 300 ml. and is filtered through 300 g. of hydrous magnesium silicate using 3 l. of methylene chloride as elutant. The first approx. 600 ml. of filtrate is discarded and the remainder is evaporated to a tan, pasty solid. The solid is crystallized from 75 ml. of 2:1 toluene:hexane solution to give a colorless solid containing a less polar by-product. The mixture is crystallized from absolute ethanol in which the by-product separates out first. The mixture is filtered and the filtrate is concentrated to dryness and the residue is crystallized again from ethanol. This process is repeated until all of the by-product is removed. The product fractions were combined and crystallized twice from 2:1 toluene:hexane to give 8.3 g. of the title compound as colorless crystals, melting point 123°–124° C.

EXAMPLE 16

Preparation of N-[4-(hexadecylamino)benzoyl]methanesulfonamide

A solution of 25.2 g. of 4-(hexadecylamino)benzoyl chloride hydrochloride and 5.8 g. of methanesulfonamide in 250 ml. of pyridine was stirred under reflux for 2 hours and then concentrated in vacuo. The residue was partitioned between water and diethyl ether; the aqueous layer acidified with 1N HCl, and the organic layer separated, dried (MgSO$_4$), and evaporated. Crystallization of the residual white solid from 60% aqueous acetic acid followed by CH$_2$Cl$_2$-hexane afforded the product as a white solid.

EXAMPLE 17

Preparation of ethyl 4-(hexadecylamino)benzoyl carbazate

The 21.1 g. of 4-(hexadecylamino)benzoyl chloride hydrochloride in methylene chloride was added to a stirred solution of 11.0 g. of ethyl carbazate in 200 ml. of ether and the very thick mixture was stirred for 1 hour at ambient temperature, diluted with 200 ml. of water and filtered. The white solid was partitioned between 200 ml. water and 1 l. of 4:1 CH$_2$Cl$_2$:ethyl acetate. The organic layer was separated, washed with 200 ml. of 1N NaOH solution and 200 ml. of H$_2$O, dried (MgSO$_4$), and concentrated in vacuo. Recrystallization of the residual white solid twice from acetone-hexane gave the product.

EXAMPLE 18

Preparation of N-[4-(hexadecylamino)benzoyl]urea

The 12.6 g. of 4-(hexadecylamino)benzoyl chloride hydrochloride in methylene chloride is added to 5 g. of sodium urea in 30 ml. of acetone and the mixture is stirred at 20° C. for 18 hours. Dilute alkali is added and the solid washed with alkaline aqueous acetone. Recrystallization from ethanol gives pure white crystals of product.

EXAMPLE 19

Preparation of 4-(hexadecylamino)benzoyl hydroxamic acid

The 16.7 g. of 4-(hexadecylamino)benzoyl chloride hydrochloride in methylene chloride is added at 5° C. to a mixture of 2.8 g. of hydroxyamine hydrochloride, 4.2 g. of sodium carbonate, and 120 ml. of ether. The mixture is stirred 3 hours after adding 10 ml. of water. After the addition of 150 ml. of water, the solvents are aerated off. The crystalline product is recrystallized from acetonitrile.

EXAMPLE 20

Preparation of O-methyl 4-(hexadecylamino)benzoyl hydroxamic acid

This substance is prepared by the method of Example 19 using a molar equivalent of methoxylamine.

EXAMPLE 21

Preparation of 3-[4-(hexadecylamino)benzoyl]-4-carboethoxythiazolidine

One-tenth mole of 4-(hexadecylamino)benzoyl chloride hydrochloride in methylene chloride is added to a solution of 0.1 mole of ethyl thiazolidine-4-carboxylate in chloroform containing two equivalents of triethylamine. After 5 hours at 20° C. the solution is filtered and evaporated to a white solid which is recrystallized from acetonitrile.

EXAMPLE 22

Preparation of 3-[4-(hexadecylamino)benzoyl]-4-carboxythiazolidine

By means of the alkaline hydrolysis method of Example 7, the ethyl ester of Example 21 is converted to the subject carboxylic acid. This acid is also prepared using the procedure of Example 21 except that the acylation of the thiazolidine-4-carboxylic acid is carried out in aqueous acetone sodium bicarbonate solution.

EXAMPLE 23

Preparation of 4-(hexadecylamino)benzoyl benzylamide

A solution of 21.1 g. of 4-(hexadecylamino)benzoyl chloride hydrochloride in 100 ml. of methylene chloride was added during 20 minutes to a stirred solution of 11.0 g. of benzylamine in 100 ml. of diethyl ether and the mixture was stirred 4 hours at ambient temperature and then diluted with 100 ml. of water. The white solid obtained by filtration was crystallized from ethanol.

EXAMPLE 24

Preparation of 4-(hexadecylamino)benzoylhydrazine

A mixture of 6.59 g. of methyl 4-(hexadecylamino)-benzoate, 100 ml. of diethylene glycol, and 45 ml. of 95% hydrazine was heated and stirred in an oil bath at 125° C. under nitrogen for 3 hours and cooled to room temperature. The separated crystals were collected in a suction funnel and washed with ethanol several times and dried in air to give 7.6 g. of white crystals. The crystals were dissolved in 140 ml. of boiling ethanol and recrystallized to give 5.95 g. of fine white crystals, melting point 154°–156° C.

EXAMPLE 25

Preparation of 4-(hexadecylamino)benzoyl glycineamide

Into a solution of 4 g. of ethyl N-[4-(hexadecylamino)benzoyl]glycinate in 50 ml. of ethanol is bubbled ammonia gas until uptake ceases. The reaction is stirred at room temperature for 24 hours, then diluted with 100 ml. water. The precipitate is collected, washed with water, and dried. Crystallization from methyl cellosolve yields white crystals.

EXAMPLE 26

Preparation of sodium p-[4-(hexadecylamino)benzamido]benzenesulfonate

A methylene chloride solution of N-trifluoroacetyl-4-(hexadecylamino)benzoyl chloride (4.8 g.) is added to a solution of 1.8 g. of sulfanilic acid in 1N sodium hydroxide at 0° C. After 3 hours, the solution is warmed to 60° C. briefly and the whole evaporated to dryness. The residue is extracted with a small amount of cold water and the resulting white solid crystallized from aqueous ethanol.

EXAMPLE 27

Preparation of N-benzoyl-[4-(hexadecylamino]benzamide

One gram of a 50% oil dispersion of sodium hydride was washed with petroleum ether by decantation, dried, and suspended in 5 ml. of tetrahydrofuran. To this stirred mixture was added a solution of 2.42 g. of benzamide in 5 ml. of tetrahydrofuran in one portion. An initial hydrogen evolution was observed. While stirring (30 min.), NaH gradually disappeared and it became a white-milky turbid mixture. Then a solution of 0.9 g. of N-trifluoroacetyl-4-(hexadecylamino)benzoyl chloride in 3 ml. of tetrahydrofuran was added dropwise during 5 minutes. No apparent change was observed. The whole milky mixture was stirred at room temperature under nitrogen for one hour. The whole reaction mixture was poured into water and extracted with ether twice. The ether extract was washed with water, brine, and dried over $Na_2SO_4$. After evaporation of solvent, it gave a pale yellow solid. The solid was dissolved in hot ether/acetonitrile (50/50) and let stand overnight at room temperature whereby 370 mg. of pure nice crystal was collected. The solids from mother liquor was recrystallized from hot acetonitrile to give 390 mg. of pale yellow crystals, which were freely soluble in $CHCl_3$ or ether at room temperature, but not soluble in absolute ethanol at room temperature.

EXAMPLE 28

Preparation of N-carbobenzyloxy-4-(hexadecylamino)benzoyl chloride

To 15 g. of 4-(n-hexadecylamino)benzoic acid in 200 ml. warm chloroform is added 15 g. sodium carbonate in 150 ml. water. To the vigorously stirred solution is added 10 g. carbobenzoyl chloride. After 2 hours stirring at 40° C., the layers are separated, washed three times with 1N hydrochloric acid, dried, and evaporated to an oil. The oil is dissolved in 300 ml. toluene, treated with 15 ml. of thionyl chloride, and the solution is refluxed for 5 hours. The solvents are evaporated and the residue is dissolved three times in toluene, evaporating each time to yield a viscous, orange oil.

EXAMPLE 29

Preparation of 4-(hexadecylamino)benzoyl piperidide

To a warm solution of N-carbobenzoyloxy-N-(4-n-hexadecylamino)benzoyl chloride and 1.3 g. of triethylamine in 100 ml. ether is added 1.2 g. of piperidine. An immediate precipitate forms, but the mixture is refluxed for one hour and filtered white hot. The solid is washed several times with hot ether, then the ether is evaporated to yield a white solid. The product is dissolved in tetrahydrofuran (100 ml.) and hydrogenated over 600 mg. 10% Pd on carbon at 50 psi. until hydrogen up-take stops. The catalyst is filtered off. The solution is evaporated, and the residue is crystallized from acetic acid to yield the title compound as a crystalline mass.

EXAMPLE 30

Preparation of 4-(hexadecyl)aminobenzoyl pyrrolidine

A solution of 6.0 g. of N-carbobenzyloxy-N-(4-n-hexadecylamino)benzoyl chloride and 1.2 g. triethylamine in 100 ml. warm ether is treated with 1.1 g. of pyrrolidine. After 1 hour at reflux, the precipitate is filtered off and washed with warm ether. After evaporation to dryness, the intermediate is dissolved in 50 ml. 30% hydrobromic/acetic acid and warmed at 50° for 2 hours. The solvents are evaporated and the product is partitioned between methylene chloride and water. The layers are separated and the methylene chloride is evaporated. The residue is crystallized from acetone to yield colorless crystals.

EXAMPLE 31

Preparation of N-trifluoroacetyl-4-(hexadecylamino)benzoyl chloride

To a stirred, ice-cold suspension of 9 g. of 4(n-hexadecylamino)benzoic acid in 100 ml. of dimethoxyethane and 16 ml. of pyridine is added 18 ml. of trifluoroacetic anhydride. The solution is stirred at 0° C. for 30 min. at room temperature. The solution is diluted with 300 ml. of ether and 100 g. of ice. After stirring vigorously for 15 min., the phases are separated, the ether solution is washed with brine, dried, and evaporated to a white, amor phouse solid.

To 9.2 g. of the above product in 30 ml. of methylene chloride and 0.5 ml. of dimethylformamide is added 5.7 ml. of thionyl chloride. After 20 hours at reflux, the solvents are evaporated to yield a light yellow, mobile oil.

EXAMPLE 32

Preparation of N-[4-(hexadecylamino)benzoyl]alanine

A solution of 4.75 g. of N-trifluoroacetyl-4-(n-hexadecylamino)benzoyl chloride and 1.2 g. of triethylamine in 200 ml. of warm ether is treated with 1.55 g. alanine ethyl ester and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields the diethyl tartrate as a white, crystalline solid.

EXAMPLE 33

Preparation of N-(t-butyloxycarbonyl)-4-(n-hexadecylamino)benzoyl-imidazole

A solution of 10 g. of 4-(n-hexadecylamino)benzoic acid in 100 ml. dioxane is treated with 4.0 g. of t-butylazidoformate and 10 ml. pyridine. After stirring at room temperature for 18 hours, the protected amidoacid is precipitated from solution by addition of 150 ml. of water. The product is collected and thoroughly dried. The crude product is dissolved in 200 ml. of a mixture consisting of methylene chloride/dimethoxy ethane/pyridine (1:4:1), and to this is added 5.4 g. of 1,1′-carbonyldiimidazoye. The solution is stirred overnight at room temperature and the solvents are evaporated to yield the title compound as a thick, orange oil.

EXAMPLE 34

Preparation of N-[4(hexadecylamino)benzoyl]imidazole

To 4.3 g. of N-(t-butoxycarbonyl)-4-(hexadecylamino)benzoyl-imidazole in 50 ml. of hot chloroform is added 5 ml. of anhydrous trifluoroacetic acid. After 30 minutes at 40°-60° C., the solution is cooled and carefully neutralized with diisopropylethylene. The white product is recrystallized from acetonitrile.

EXAMPLE 35

Preparation of 4-(hexadecylamino)benzoyl-2,3-dihydroxypropylamide

To a mixture containing 4.3 g. of N-(t-butyloxycarbonyl)-4-(n-hexadecylamino)benzoyl-imidazole, 50 ml. of chloroform, and 50 ml. of 5N sodium hydroxide is added 1.1 g. of 3-amino-1,2-propanediol. The solution is vigorously stirred for 24 hours, the layers are separated, and the chloroform solution is washed once with 50 ml. of 1N sodium hydroxide. The solvent is evaporated and the residue is heated for 30 minutes at 40° C. in 50 ml. of anhydrous trifluoroacetic acid. The solvent is again evaporated and the oil is crystallized from acetone to yield light yellow crystals of ethyl β-(n-hexadecylamino)benzoyl acrylate.

EXAMPLE 36

Preparation of 4-(hexadecylamino)benzoyl-pyrrolidine

To a gently refluxing solution of 8 g. of 4-(hexadecylamino)benzoic acid in 200 ml. of $CH_2Cl_2$ and 50 ml. of glyme was bubbled hydrogen chloride gas for 15 minutes. The refluxing condenser was attached to a $CaCl_2$ drying tube. The hydrochloride salt precipitated out immediately. The white solid mixture was cooled and allowed to stand overnight at room temperature. Then, 20 ml. of thionyl chloride was added and the mixture was refluxed for 2 hours. The resulting pale brown solution was rotary evaporated to dryness. Toluene was added and evaporated to dryness again. This was repeated twice followed by vacuum pump to afford a red-brownish viscous liquid.

To a solution of 1.25 g. of pyrrolidine, 1.25 ml. of triethylamine and 0.3 g. of 4-dimethylaminopyridine in 50 ml. of ether, cooled in an ice-bath, was added dropwise a solution of 4 g. of the acid chloride in 25 ml. of diethyl ether using a dropping funnel under nitrogen. After addition, the mixture was stirred at room temperature overnight. Diluted with water and the separated ether layer was washed with water again, brine and dried over $MgSO_4$. Upon standing, lots of crystal separated out from the dried ether solution. The ether solution was concentrated by blowing nitrogen under mild heat. The solids were collected and recrystallized from hot ether to give 1.2 g. of crystals (white) m.p. 82°-83° C.

EXAMPLE 37

Preparation of 2,3-dihydroxypropyl-4-hexadecylaminobenzamide

A slurry of 8.0 g. of 4-(hexadecylamino)benzoic acid hydrochloride in 175 ml. of $CH_2Cl_2$ and 50 ml. of glyme containing 10 ml. of thionyl chloride was heated at reflux for 2 hours. The clear solution was concentrated in vacuo giving 9.5 g. of an amber oil. This oil was diluted with 50 ml. of pyridine containing 0.1 g. of 4-dimethylaminopyridine and 9.1 g. of 3-amino-1,2-propandiol. The reaction was stirred for two days at room temperature. The solution was partitioned between ether and water. The water phase was extracted twice more with 100 ml. of chloroform and ether. The combined organic layer was extracted with water, dried over $MgSO_4$ and evaporated to a tacky solid. The solid was recrystallized from acetone-water and a second time from benzene. A small sample was recrystallized from acetonitrile, m.p. 121°-122° C.

EXAMPLE 38

Preparation of 15-methylhexadecyl bromide

A solution of 3-methylbutylmagnesium bromide is prepared by treating 15.1 g. of 3-methylbutyl bromide with 2.7 g. magnesium turnings in 50 ml. dry tetrahydrofuran. The resultant Grignard reagent is dropwise added to a cold (−10° C.) solution of 36.1 g. of 1,12-dibromododecane and 0.2 g. of $Li_2CuCl_4$ in 75 ml. dry tetrahydrofuran. The solution is stirred for 1 hour, evaporated, and fractionally distilled in vacuo to yield 15-methylhexadecyl bromide as a colorless liquid.

EXAMPLE 39

Preparation of ethyl 4-(15-methylhexadecyl)aminobenzoate

A mixture of 5 g. of 15-methylhexadecyl bromide and 5.2 g. of ethyl 4-aminobenzoate in 50 ml. hexamethylphosphoramide is heated for 17 hours at 120° C. The cooled solution is diluted with an equal volume of water and the resultant precipitate is filtered, washed with 100 ml. of 50% ethanol, dried, and crystallized from ethanol to yield a colorless crystalline solid.

EXAMPLES 40-91

The compounds tabulated below are prepared by using the molar equivalent of the corresponding intermediate in the procedure of the example designated in the table.

| Example No. | 4-(Hexadecylamino)benzamide Derivatives | |
|---|---|---|
| | Resulting From Procedure Example No. | Product 4-(Hexadecylamino)-benzoyl- |
| 40 | 3 | propargylamide |
| 41 | 1 | ethylamide |
| 42 | 4 | pyrrolidide |
| 43 | 4 | hexamethyleneimide |
| 44 | 5 | $\Delta^3$-pyrroline-1-imide |
| 45 | 1 | diethylamide |
| 46 | 1 | isobutylamide |
| 47 | 5 | allylamide |
| 48 | 20 | ethoxyamide |
| 49 | 4 | 2-methylpiperidide |
| 50 | 4 | 4-methylpiperidide |
| 51 | 4 | 3,5-dimethylpiperidide |
| 52 | 4 | 3-hydroxymethylpiperidide |
| 53 | 14 | ethanesulfonamide |
| 54 | 24 | 2,2-dimethylhydrazide |
| 55 | 24 | 2-ethylhydrazide |
| 56 | 6 | 2-amino-2-carboethoxy-ethylamide |
| 57 | 8 | 2-amino-2-carboxyethylamide |
| 58 | 7 | 2-amino-2-carboxyethylamide |
| 59 | 18 | acetylimide |
| 60 | 18 | isobutyrylimide |
| 61 | 8 | 1,2-dicarboxyethylamide |
| 62 | 5 | cyclohexylamide |
| 63 | 5 | cyanomethylamide |
| 64 | 21 | 3-thiazolidide |
| 65 | 18 | 3,3-dimethylureide |
| 66 | 27 | ethanesulfonylhydrazide |
| 67 | 4 | 2,5-dimethylpyrrolide |
| 68 | 4 | 3-hydroxypyrrolide |
| 69 | 37 | 2-hydroxypropylamide |
| 70 | 35 | 3-hydroxypropylamide |
| 71 | 29 | morpholide |
| 72 | 30 | 4-n-propylpiperazine |
| 73 | 5 | 4-methylpiperazine |
| 74 | 3 | 4-hydroxyethylpiperazine |
| 75 | 6 | ethyl 3-aminobutyrate |
| 76 | 7 | 3-aminobutyric acid |
| 77 | 6 | methyl $\beta$-alanine |
| 78 | 37 | 1-hydroxy-2-butylamide |
| 79 | 5 | 2-(1-piperidyl)ethylamide |
| 80 | 5 | 2-hydroxyethylamide |
| 81 | 5 | 2-dimethylaminoethylamide |
| 82 | 37 | 1,3-dihydroxy-2-propylamide |
| 83 | 3 | glucamine |
| 84 | 4 | N—methylglucamine |
| 85 | 32 | 2-furylmethylamide |
| 86 | 36 | 3-pyridylmethylamide |
| 87 | 35 | 4-pyridylmethylamide |
| 88 | 30 | 2-pyridylmethylamide |
| 89 | 4 | 3-methylpiperidide |
| 90 | 29 | 2-hydroxymethylpiperidide |
| 91 | 35 | 2,6-dimethylpiperidide |

EXAMPLE 92

Preparation of 4-(15-methylhexadecyl)aminobenzoic acid

A solution of 3.5 g. of ethyl 4-(15-methylhexadecyl)aminobenzoate and 1.7 g. of 85% potassium hydroxide in 50 ml. of 95% ethanol is heated at reflux for 5 hours. The warm solution is diluted with 100 ml. water and adjusted to pH 5 with 37% hydrochloric acid. The precipitate is collected, dried, and crystallized from acetic acid to yield the title compound as an amorphous, cream-colored solid.

EXAMPLE 93

Preparation of 14-methylpentadecyl bromide

By a procedure analagous to that described in Example 1, 3-methylbutylmagnesium bromide in tetrahydrofuran is reacted with 34.5 g. of 1,11-dibromoundecane and 0.2 g. of Li$_2$CuCl$_4$ in 75 ml. tetrahydrofuran. After one hour stirring at $-10°$ C., the solution is evaporated and the resultant oil is distilled in vacuo to yield the colorless 14-methyl pentadecyl bromide.

EXAMPLE 94

Preparation of 4-(15-methylhexadecyl)aminobenzoyl chloride hydrochloride

This acid chloride is prepared from the acid of Example 92 using the procedure of Example 2.

EXAMPLE 95

Preparation of ethyl 4-(14-methylpentadecyl)aminobenzoate

A solution of 10 g. of 14-methylpentadecyl bromide and 10.8 g of ethyl 4-aminobenzoate in 75 ml. hexamethylphosphoramide is heated at 120° C. for 17 hours. The cooled solution is diluted with 100 ml. water, filtered, and the residue is washed with 100 ml. 50% ethanol-water. The product is dried, then crystallized from ethanol to yield ethyl 4-(14-methylpentadecyl)aminobenzoate as colorless crystals.

EXAMPLE 96

Preparation of 4-(14-methylpentadecyl)aminobenzoic acid

A 4 g. sample of ethyl 4-(14-methylpentadecyl)aminobenzoate is hydrolized with 2.0 g. of 85% potassium hydroxide in 60 ml. 95% ethanol by refluxing the solution for 5 hours. The solution is cooled, diluted with 100 ml. water, and acidified to pH 4.5 with 37% hydrochloric acid. The precipitate is collected and dried in vacuo to yield the title compound as a white powder.

EXAMPLE 97

Preparation of 13,13-dimethyltetradecyl bromide

A solution of t-butylmagnesium bromide is prepared by reacting 13.7 g. of t-butyl bromide with 2.67 g. of magnesium turnings in 50 ml. dry tetrahydrofuran. The solution of Grignard reagent is dropwise added to a stirred, cold ($-10°$ C.) solution of 36.1 g. of 1,12-dibromododecane and 0.2 g. of Li$_2$CuCl$_4$ in 75 ml. dry tetrahydrofuran at a rate such that the reaction temperature does not exceed $-5°$ C. After one additional hour of stirring at $-10°$ C., the solvent is evaporated and the resultant liquid is fractionated in vacuo to yield 13,13-dimethyltetradecyl bromide as a colorless liquid.

EXAMPLE 98

Preparation of 15,15-dimethylhexadecyl bromide

Prepared using 4,4-dimethylpentylbromide in the procedure of Example 97 above instead of t-butylbromide.

EXAMPLE 99

Preparation of ethyl 4-(13,13-dimethyltetradecyl)aminobenzoate

A solution of 10 g. of 13,13-dimethyltetradecyl bromide and 10.8 g. of ethyl 4-aminobenzoate in 75 ml. hexamethylphosphoramide is heated at 110° C. for 17 hours. The cooled solution is diluted with 100 ml. water, filtered, and the residue is washed in portions with 100 ml. 50% ethanol-water. After drying, the product is crystallized from ethanol to yield ethyl 4-(13,13-dimethyltetradecyl)aminobenzoate as colorless crystals.

EXAMPLE 100

Preparation of 4-(13,13-dimethyltetradecyl)aminobenzoic acid

A solution of 5 g. of ethyl 4-(13,13-dimethyltetradecyl)aminobenzoate in 75 ml. 95% ethanol is saponified with 2.5 g. of 85% potassium hydroxide by refluxing for 5 hours. The warm solution is diluted with 150 ml. water and adjusted to pH 5 with 37% hydrochloric acid. The precipitate is filtered, washed with water, dried in vacuo and crystallized from acetic acid to yield the title compound as a cream-colored, amorphous solid.

EXAMPLES 101–108

The following tabulated 4-(alkylamino)benzamides are prepared by the procedures indicated and using the corresponding acid chlorides

| Example No. | Synthesis By Procedure of Example | 4-(Alkylamino)benzamide | |
|---|---|---|---|
| | | Alkyl Group | Amide Moiety |
| 101 | 4 | 15-methylhexadecyl | piperidide |
| 102 | 29 | 14-methylpentadecyl | piperidide |
| 103 | 37 | 14-methylpentadecyl | 2,3-dihydroxypropylamide |
| 104 | 35 | 13,13-dimethyltetradecyl | 2,3-dihydroxypropylamide |
| 105 | 4 | 1-ethyltetradecyl | piperidide |
| 106 | 4 | 1,4-diethyloctyl | piperidide |
| 107 | 29 | 5,5-dimethylhexyl | piperidide |
| 108 | 30 | 1-ethyltetradecyl | 2,3-dihydroxypropylamide |

EXAMPLE 109

Preparation of 3-bromopropyl-4-hexadecylaminobenzamide

To a slurry of 21.80 g. of 2-bromopropylamine hydrobromide in 200 ml. of glyme at 3° C. was added a solution of 23.96 g. of 4-(hexadecylamino)benzoyl chloride hydrochloride in 65 ml. of glyme, concurrently with 26 ml. of triethylamine diluted to 39 ml. with glyme. The solution was warmed to reflux and 0.2 g. of 4-dimethylaminopyridine was added. The solution was heated for four hours and cooled overnight. The solid was removed and the mother liquor diluted with 200 ml. of water giving 12.94 g. (55%). The solid was recrystallized from cyclohexane (7.7 g.). A 500 mg. aliquot was recrystallized from acetonitrile (0.43 g.). A one gram sample was loaded onto 85 gm. of silica gel and two components removed by elution with chloroform. The largest (0.6 g.) component was recrystallized from acetonitrile (0.4 g.) m.p. 115°–115° C.

EXAMPLE 110

Preparation of 2-[4-(hexadecylamino)phenyl]-5,6-dihydro[4H]-1,3-oxazine

To 0.4 g, of NaH in 100 ml. of glyme was added 2.14 g. of N-(3-bromopropyl)-4-(n-hexadecylamino)benzamide and 12 ml. of triethylamine. The turbid solution was heated to reflux for 20 hours. The solution was diluted with 100 ml. of water and cooled overnight. The solid was collected, washed with water and oven dried giving 2 g. of solid which gave a negative AgNO$_3$ test and halogen flame test. This solid was recrystallized from cyclohexane giving 1.68 g. of solid, m.p. 95°–96° C. A 200 mg. aliquot was recrystallized from 10 ml. of acetonitrile giving crystals, m.p. 95°–96° C.

EXAMPLE 111

Preparation of 2-(4-aminophenyl)-4,4-dimethyl-2-oxazoline

To a solution of 9.5 g. of N-(1,1-dimethyl-2-hydroxyethyl)-4-aminobenzamide in 100 ml. of DME was added gaseous HCl such that all of the starting amide came out of solution. The solvent was removed and 30 ml. of thionyl chloride added. This solution was stirred for 2 days at 5° C. The excess thionyl chloride was removed. The amber liquid was then poured into 200 ml. of CH$_2$Cl$_2$ and neutralized with 20% NaOH with cooling. The solution was extracted with diethyl ether and the ether layer dried over MgSO$_4$. The combined ether layer was filtered and concentrated to a solid; 5.75 g. This solid was preabsorbed on 25 g. of silica III and placed on 425 g. of silica (in a column). Elution with ether gave 3.7 g. of product which was recrystallized from CH$_2$Cl$_2$-hexane (1:1) and acetonitrile, m.p. 227°–230° C.

EXAMPLE 112

Preparation of 2-[4-(hexadecylamino)phenyl]oxazoline

To a slurry of 15 g. of 2-bromoethylamine hydrobromide in 150 ml. of glyme was added simultaneously solutions of 31 g. of 4-(hexadecylamino)benzoyl chloride hydrochloride in 60 ml. of glyme and 50 cc. of triethylamine (dropwise). Upon addition of 0.5 g. of 4-dimethylaminopyridine the "solution" was stirred at room temperature overnight. The solution was refluxed for one hour and filtered. The solid was oven dried and portitioned between CH$_2$Cl and water. The layers were separated and the organic phase dried over MgSO$_4$. The organic layer was concentrated to about 100 ml. and 4-(hexadecylamino)benzoyl chloride hydrochloride diluted with an equal volume of hexane. The combined product (4.15 g.) was preabsorbed on 40 g. of silica III and placed on a column of silica III (800 g.). Fractions were collected by U.V. (CH$_2$Cl$_2$-EtOH 97-3) and samples with the same TLC combined giving 3.8 g. after recrystallization from cyclohexane. A 210 mg. sample was recrystallized from acetonitrile and CH$_2$Cl$_2$/hexane giving 149 mg., m.p. 123°–125° C.

EXAMPLE 113

Preparation of 50 mg. Tablets

| Per Tablet | | Per 10,000 Tablets |
|---|---|---|
| 0.050 gm. | 4-(n-hexadecylamino)benzamide | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 |
| 0.150 gm. | | 1490 gm. |

The 4-(n-hexadecylamino)benzamide, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 114

Preparation of Oral Suspension

| Ingredient | Amount |
| --- | --- |
| N—[4-(n-tetradecylamino)benzoyl]morpholine | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs ad | 100 ml. |

The sorbitol solution is added to 40 ml. of distilled water and the N-[4-(n-tetradecylamino)benzoyl]morpholine is suspended therein. The saccharin, sodium benzoate, flavor and dye are added and dissolved. The volume is adjusted to 100 ml. with distilled water. Each ml. of syrup contains 5 mg. of N-[4-(n-tetradecylamino)-benzoyl]morpholine.

EXAMPLE 115

Preparation of N-[4-(hexadecylamino)benzoyl]-2-aminoethanesulfonic acid

To a stirred solution of 2.50 g. of taurine and 5.6 ml. of triethylamine in 22.5 ml. of water is added 5.55 g. of N-[p-(2,2,2-trifluoro-N-hexadecylacetamido)benzoyloxy]succinimide as a solution in 45 ml. of ethanol. After 24 hours, the mixture is treated with 20 ml. of 2.0M sodium hydroxide and 25 ml. of water. After stirring for 10 min., the mixture is acidified with dilute hydrochloric acid, and the crude product is collected by filtration. Recrystallization affords the title compound as a white solid, m.p. 190°-220° C.

EXAMPLE 116

Preparation of p-[p-(n-hexadecylamino)benzamido]benzoic acid

To a stirred solution of 3.62 g. of ethyl p-[p-(2,2,2-trifluoro-N-hexadecylacetamido)benzamido]benzoate in 72 ml. of ethanol was added a solution of 1.44 g. of sodium hydroxide in 18 ml. of water and the resulting mixture was heated under reflux for 30 min. The mixture was allowed to cool, acidified with dilute hydrochloric acid, and filtered. The white solid was recrystallized from acetonitrile.

EXAMPLE 117

Preparation of ethyl 4-[p-(2,2,2-trifluoro-N-hexadecylacetamido)benzamido]benzoate To a stirred solution of 1.65 g. of ethyl p-aminobenzoate and 1.6 ml. of pyridine in 5 ml. of dichloromethane at 0° C. is added a solution of 4.75 g. of p-(2,2,2-trifluoro-N-hexadecylacetamido)benzoyl chloride in 10 ml. of dichloromethane. After 20 hours at ambient temperature the solution is diluted with dichloromethane and washed with water and sodium bicarbonate solution. The residue obtained on evaporation of solvent is recrystallized from hexane-ether to give a white, crystalline solid, m.p. 91°-93° C.

EXAMPLE 118

Preparation of N-[p-(2,2,2-trifluoro-N-hexadecylacetamido)benzoyloxy]succinimide To a stirred ice-cold solution of 18.3 g. of p-(2,2,2-trifluoro-N-hexadecylacetamido)benzoic acid in 80 ml. of dioxane is added successively 4.84 g. of N-hydroxysuccinimide and 9.16 g. of dicylohexylcarbodiimide. After 18 hours at 0°-5° C. the mixture is stirred vigorously for one hour with hexane and water and filtered. The hexane layer is washed with water, dried over magnesium sulfate, and concentrated to give an oil.

EXAMPLE 119

Preparation of N-trifluoroacetyl-4-(hexadecylamino)benzoic acid

To a stirred, ice-cold suspension of 0.90 g. of 4-(n-hexadecylamino)benzoic acid in 10 ml. of dimethoxyethane and 1.6 ml. of pyridine is added 1.8 ml. of trifluoroacetic anhydride. The solution is stirred at 0° C. for 30 min., then 30 min. at room temperature. The solution is diluted with 30 ml. of ether and 10 g. of ice. After stirring vigorously for 15 min., the phases are separated, the ether solution is washed with brine, dried, and evaporated to a white amorphous solid. Recrystallization from hexane affords the title compound as a crystalline solid, m.p. 50°-53° C.

EXAMPLE 120

Preparation of N-[4-(hexadecylamino)benzoyl]-2-aminoisobutyric acid

To a stirred solution of 103 mg. of 2-aminoisobutyric acid and 4.5 ml. of triethylamine in 1.5 ml. of water is added a solution of 550 mg. of N-[N-trifluoroacetyl-4-(hexadecylamino)benzoyloxy]succinimide in 4.5 ml. of ethanol. The mixture is stirred for 23 hours at room temperature, treated with 2 ml. of 2N sodium hydroxide solution, and then acidified. The mixture is diluted with water and then filtered. Recrystallization from ether-hexane affords the title compound as a white solid.

EXAMPLES 121-128

The compounds tabulated below are prepared by using the molar equivalent of the corresponding intermediate in the procedure of the example designated in the table.

| | 4-(Hexadecylamino)benzamide Derivatives | |
| --- | --- | --- |
| Example No. | Resulting from the Pro-Procedure of Example Number | Product 4-(Hexadecylamino)benzoyl- |
| 121 | 115 | 1-sulfo-2-propylamide |
| 122 | 117 | anilide |
| 123 | 117 | 4-chloroanilide |
| 124 | 117 | 2,5-dimethyl-3-pyrroline-1-imide |
| 125 | 8 | β-alanine |
| 126 | 8 | serine |
| 127 | 8 | 6-aminocaproic acid |
| 128 | 29 | 2-β-hydroxyethylpiperidide |

EXAMPLES 129-132

The following tabulated 4-(alkylamino)benzamides are prepared by the procedures indicated and using the corresponding acid chlorides.

| Example No. | Synthesis by Procedure of Example No. | 4-(Alkylamino)benzamide Alkyl Group | Amide Moiety |
|---|---|---|---|
| 129 | 4 | 13,13-dimethyltetradecyl | piperidide |
| 130 | 4 | 2,4,6,8-tetramethylnonyl | piperidide |
| 131 | 4 | 4-(N—methylhexadecyl) | piperidide |
| 132 | 4 | 14-methylpentadecyl | piperidide |

I claim:

1. The method of treating hyperlipidemia and hyperlipoproteinemia and/or favorably altering the lipoprotein pattern in a mammal which comprises administering to said mammal a therapeutically effective amount therefor of a compound selected from the group consisting of those of the formula:

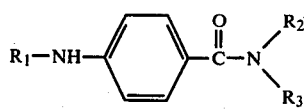

wherein $R_1$ is a straight chain or branched alkyl group of the formula $C_nH_{2n+1}$ wherein n is an integer from 8 to 19, inclusive; $R_2$ is selected from the group consisting of hydrogen, lower alkyl, carboxy lower alkyl, carboalkoxy lower alkyl, lower alkanoyl, carbamoyl, di(-lower alkyl)carbamoyl, lower alkanesulfonyl, benzenesulfonyl, sodium sulfo lower alkyl, sulfo lower alkyl, lower alkenyl, lower alkynyl, cyclohexyl, phenyl lower alkyl and ω-hydroxy lower alkyl; $R_3$ is selected from the group consisting of hydrogen, lower alkyl, hydroxy, lower alkoxy, halo lower alkyl, phenyl, carboxyphenyl, chlorophenyl, sodium sulfophenyl, pyridyl, pyridyl lower alkyl, mono- and poly-hydroxy lower alkyl, ω-lower alkoxy lower alkyl, ω-di(lower alkyl)amino lower alkyl, ω-piperidino lower alkyl, ω-pyrrolidino lower hydroxy alkyl, amino, di(lower alkyl)amino, lower alkanoylamino, lower alkanesulfonylamino, N-piperidyl, benzenesulfonylamino, and 4-lower alkyl-1-piperazino; and $R_2$ and $R_3$ taken together with the associated N(itrogen) is selected from the group consisting of pyrrolidino, piperidino, morpholino, hexamethyleneimino, 4-lower alkylpiperidino, 4-lower alkyl-1-piperazino, 4-phenylpiperazino, 3-pyrrolinyl, $\Delta^3$-piperidino, 4-(carboethoxy or carboxy)-3-thiazolidinyl, and 4-carboethoxy-3-oxazolidinyl; and the pharmacologically acceptable acid-addition salts thereof.

2. The method according to claim 1 wherein $R_1$ is n-hexadecyl and —$NR_2R_3$ is piperidino.

3. The method according to claim 1 wherein $R_1$ is n-hexadecyl, $R_2$ is hydrogen, and $R_3$ is —$SO_2C_6H_5$.

4. The method according to claim 1 wherein $R_1$ is n-hexadecyl, $R_2$ is hydrogen, and $R_3$ is —$SO_2C_6H_4CH_3$—4.

5. The method according to claim 1 wherein $R_1$ is nhexadecyl, $R_2$ is hydrogen, and $R_3$ is —$SO_2CH_3$.

6. The method according to claim 1 wherein $R_1$ is n-hexadecyl, $R_2$ is hydrogen, and $R_3$ is —$CH_2CHOHCH_2OH$.

7. The method according to claim 1 wherein $R_1$ is n-hexadecyl, $R_2$ is hydrogen, and $R_3$ is —$CH_2CO_2H$.

8. The method according to claim 1 wherein $R_1$ is n-hexadecyl, $R_2$ is hydrogen, and $R_3$ is —$CH_2CH_2SO_3H$.

9. The method according to claim 1 wherein $R_1$ is n-hexadecyl, $R_2$ is hydrogen, and $R_3$ is benzoyl.

10. The method according to claim 1 wherein $R_1$ is n-hexadecyl, $R_2$ is hydrogen, and $R_3$ is —NH—CO—CH_3.

11. The method according to claim 1 wherein $R_1$ is n-hexadecyl, $R_2$ is hydrogen, and $R_3$ is allyl.

12. The method according to claim 1 wherein $R_1$ is n-hexadecyl and —$NR_2R_3$ is piperidino.

13. The method according to claim 1 wherein $R_1$ is n-hexadecyl, $R_2$ is hydrogen, and $R_3$ is —$SO_2C_6H_5$.

14. The method according to claim 1 wherein $R_1$ is n-hexadecyl, $R_2$ is hydrogen, and $R_3$ is —$SO_2C_6H_4CH_3$—4.

15. The method according to claim 1 wherein $R_1$ is nhexadecyl, $R_2$ is hydrogen, and $R_3$ is —$SO_2CH_3$.

16. The method according to claim 1 wherein $R_1$ is n-hexadecyl, $R_2$ is hydrogen, and $R_3$ is —$CH_2CHOHCH_2OH$.

17. The method according to claim 1 wherein $R_1$ is n-hexadecyl, $R_2$ is hydrogen, and $R_3$ is —$CH_2CO_2H$.

18. The method according to claim 1 wherein $R_1$ is n-hexadecyl, $R_2$ is hydrogen, and $R_3$ is —$CH_2CH_2SO_3H$.

19. The method according to claim 1 wherein $R_1$ is n-hexadecyl, $R_2$ is hydrogen, and $R_3$ is benzoyl.

20. The method according to claim 1 wherein $R_1$ is n-hexadecyl, $R_2$ is hydrogen, and $R_3$ is —NH—CO—CH_3.

21. The method according to claim 1 wherein $R_1$ is n-hexadecyl, $R_2$ is hydrogen, and $R_3$ is allyl.

22. An antiatherosclerotic composition in dosage-unit form useful for treating hyperlipidemia and hyperlipoproteinemia and/or favorably altering the lipoprotein pattern in mammals comprising from about 50 mg. to about 250 mg. per dosage unit of a compound selected from the group consisting of those of the formula:

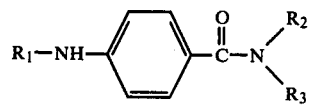

wherein $R_1$ is a straight chain or branched alkyl group of the formula $C_nH_{2n+1}$ wherein n is an integer from 8 to 19, inclusive; $R_2$ is selected from the group consisting of hydrogen, lower alkyl, carboxy lower alkyl, carboalkoxy lower alkyl, lower alkanoyl, carbamoyl, di(-lower alkyl)carbamoyl, lower alkanesulfonyl, benzenesulfonyl, sodium sulfo lower alkyl, sulfo lower alkyl, lower alkenyl, lower alkynyl, cyclohexyl, phenyl lower alkyl and ω-hydroxy lower alkyl; $R_3$ is selected from the group consisting of hydrogen, lower alkyl, hydroxy, lower alkoxy, halo lower alkyl, phenyl, carboxyphenyl, chlorophenyl, sodium sulfophenyl, pyridyl, pyridyl lower alkyl, mono- and poly-hydroxy lower alkyl, ω-lower alkoxy lower alkyl, ω-di(lower alkyl)amino lower alkyl, ω-piperidino lower alkyl, ω-pyrrolidino lower hydroxy alkyl, amino, di(lower alkyl)amino, lower alkanoylamino, lower alkanesulfonylamino, N-piperidyl, benzenesulfonylamino, and 4-lower alkyl-1-piperazino; and $R_2$ and $R_3$ taken together with the associated N(itrogen) is selected from the group consisting of pyrrolidino, piperidino, morpholino, hexamethyleneimino, 4-lower alkylpiperidino, 4-lower alkyl-1-piperazino, 4-phenylpiperazino, 3-pyrrolinyl, $\Delta^3$-piperidino, 4-(carboethoxy or carboxy)-3-thiazolidinyl, and 4-carboethoxy-3-oxazolidinyl; and the pharmacologically acceptable acid-addition salts thereof.

* * * * *